US008585930B2

(12) United States Patent
Tiwari

(10) Patent No.: US 8,585,930 B2
(45) Date of Patent: Nov. 19, 2013

(54) MONO AND BIS-ESTER DERIVATIVES OF PYRIDINIUM AND QUINOLINIUM COMPOUNDS AS ENVIRONMENTALLY FRIENDLY CORROSION INHIBITORS

(75) Inventor: Laxmikant Tiwari, Southampton (GB)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 12/882,686

(22) Filed: Sep. 15, 2010

(65) Prior Publication Data
US 2011/0003992 A1    Jan. 6, 2011

Related U.S. Application Data

(62) Division of application No. 11/763,006, filed on Jun. 14, 2007, now abandoned.

(51) Int. Cl.
| | | |
|---|---|---|
| *C23F 11/00* | (2006.01) |
| *C23F 11/10* | (2006.01) |
| *C09K 8/54* | (2006.01) |
| *C07D 239/02* | (2006.01) |
| *C07D 215/04* | (2006.01) |
| *C07D 215/10* | (2006.01) |
| *C07D 215/12* | (2006.01) |
| *C07D 213/20* | (2006.01) |

(52) U.S. Cl.
USPC ........... 252/394; 252/392; 507/242; 507/939; 544/335; 546/174; 546/341

(58) Field of Classification Search
USPC ........... 252/392, 394; 507/242, 939; 546/174, 546/341; 544/335
See application file for complete search history.

(56) References Cited

U.S. PATENT DOCUMENTS

| | | | |
|---|---|---|---|
| 2,901,430 A * | 8/1959 | Chiddix et al. ............... 507/240 |
| 4,218,234 A | 8/1980 | Bartha et al. |
| 5,300,235 A | 4/1994 | Clewlow et al. |
| 5,322,640 A | 6/1994 | Byrne et al. |
| 5,611,992 A | 3/1997 | Naraghi et al. |
| 5,756,004 A | 5/1998 | Brezinski |
| 6,261,346 B1 | 7/2001 | Breuer et al. |
| 6,303,079 B1 | 10/2001 | Meyer |
| 6,488,868 B1 | 12/2002 | Meyer |
| 6,521,028 B1 | 2/2003 | Frenier |
| 7,057,050 B2 | 6/2006 | Meyer |

FOREIGN PATENT DOCUMENTS

| | | | |
|---|---|---|---|
| DE | 2053735 A | 5/1972 |
| RO | 85177 A2 | 9/1984 |
| RU | 2220957 C1 | 1/2004 |
| SU | 966092 | 10/1982 |
| WO | WO 03/042428 A1 | 5/2003 |
| WO | WO 2004/090064 A1 | 10/2004 |

OTHER PUBLICATIONS

Loftsson et al. ("Marine lipids as building blocks for soft quaternary ammonium compounds and their antibacterial activity" Pharmazie, 2004, 59(5), 360-364).*
Aminov et al., "Synthesis and surface-active properties of quaternary ammonium salts based on alkylchloroacetates," *Uzbekskii Khimicheskii Zhurnal*, No. 6, 1979, pp. 39-43.
Bhattacharaya et al., "Microcalorimetric and Conductivity Studies with Micelles Prepared from Multi-Headed Pyridinium Surfactants," *Langmuir*, vol. 21, No. 13, 2005, pp. 5747-5751.
Davletshin et al,. "Effect of surfactants on a peroxidase activity. II. Effect of cationic surfactants," *Bioorganicheskaya Khimiya*, vol. 24, No. 6, 1998, pp. 430-432.
Egorov et al., "Characteristics of radical polymerization in alcohols of vinyl pyridinium salts with various hydrophilic-hydrophobic balance," *Vysokomolekulyarnye Soedineniya*, vol. 23, No. 4, 1981, pp. 848-853.
Egorov et al., "Colloidal and chemical properties of N-(alkoxycarbonylinethyl)-2-methyl-5-vinylpyridinium bromides," *Viniti*, No. 4170-83, 1983, pp. 1-11.
Egorov et al., "Structure of secondary micelles of cationic surface-active monomers in water," *Kolloidnyi Zhurnal*, vol. 54, No. 1, 1992, pp. 40-44.
Gad et al., "Surface and Thermodynamic Studies of N-((octyl, dodecyl and cetyl) Oxycarbonylmethyl) Pyridinium bromide," *Monatshefte Fuer Chemie*, vol. 128, No. 12, 1997, pp. 1237-1246.

(Continued)

*Primary Examiner* — Peter F Godenschwager
(74) *Attorney, Agent, or Firm* — Edward O. Yonter; Andrew D. Sorensen

(57) ABSTRACT

A quaternary nitrogen-containing corrosion inhibitor of formula

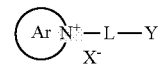

wherein

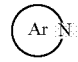

is an aromatic, nitrogen-containing ring of 5 to 14 ring atoms, optionally containing an additional N, O or S ring atom and optionally substituted with one or more alkyl, alkenyl, aryl, arylalkyl, cycloalkyl, amino, aminoalkyl, alkoxy, hydroxylalkyl, or cyano groups, or a mixture thereof; Y is a group of formula —OC(O)$R_1$ or —C(O)$R_1$; L is $C_1$-$C_{10}$ alkyl, $C_2$-$C_{10}$ alkenyl or a group of formula —$CH_2CH(OR_2)CH_2$—; $R_1$ is $C_8$-$C_{20}$ alkyl or $C_8$-$C_{20}$ alkenyl; $R_2$ is H or —C(O)$R_1$; $R_3$ and $R_4$ are independently selected from H, alkyl, alkenyl, amino, alkoxy, hydroxylalkyl and cyano; and X is Br, Cl or I is particularly useful for inhibiting corrosion in oil and gas field applications.

18 Claims, No Drawings

(56) References Cited

OTHER PUBLICATIONS

Loftsson et al., Hydrolysis kinetics and QSAR investigation of soft antimicrobial agents, *Journal of Pharmacy and Pharmacology*, vol. 57, No. 6, pp. 2005, 721-727.

Malyukova et al., "Emulsion polymerization of styrene in the presence of monomer-emulsifer N-decylaceto-2-methyl-5-vinylpyridinium bromide," *Doklady Adademii Nauk SSSR*, vol. 265, No. 2, 1982, pp. 30-33.

Pis'ko et al., "The relation between chemical structure and antimicrobial activity of the quaternary salts of esters if pyridine-, picoline-, N-methylmorpholine- and triethylaminaocetic acids," *Fiziologicheski Aktivnye Veshchestva*, No. 18, 1986, pp. 14-18.

Thorsteinsson et al., "Soft antimicrobial agents: synthesis and activity of labile environmentally friendly long chain quaternary ammonium compounds," *Journal of Medicinal Chemistry*, vol. 46, No. 19, 2003, pp. 4173-4181.

\* cited by examiner

MONO AND BIS-ESTER DERIVATIVES OF PYRIDINIUM AND QUINOLINIUM COMPOUNDS AS ENVIRONMENTALLY FRIENDLY CORROSION INHIBITORS

CROSS REFERENCE TO RELATED APPLICATION

This application is a divisional of U.S. Ser. No. 11/763,006, filed on June 14, 2007, now abandoned, which is herein incorporated in its entirety by reference.

TECHNICAL FIELD

This invention relates to novel quaternary nitrogen compounds and compositions comprising the compounds which are useful as corrosion inhibitors, particularly in oil and gas field applications and more particularly in situations where they may come into contact with the natural environment, and to a method of inhibiting corrosion using the compounds.

BACKGROUND OF THE INVENTION

Stringent environmental constraints imposed by government regulation upon the oil and gas producing industry has led to the need for new "greener' chemistries, which have less environmental impact. This environmental drive has been spearheaded by North Sea Regulators such as CEFAS, and due to their success similar programs are being implemented in other oil producing regions. Operators now demand identical levels of performance with existing treatments along with the fulfillment of the new environmental criteria for any chemicals that may be contained, for example, in rig overboard discharge.

Corrosion inhibitors are given particular attention due to their inherent design to partition into the aqueous phase. The environmental impact of a corrosion inhibitor is often defined by three criteria: biodegradation, bioaccumulation and toxicity. All three criteria have benchmarks that must be met for a chemical to be permitted for use, with different emphasis on each depending on which regulator controls the waters.

Quaternary nitrogen compounds (Quats) have been used extensively as they form a film on the surface of steel, are stable over a wide range of pH and temperature, cost effective, efficient in sour conditions and inhibit microbially induced corrosion (MIC). See, for example, U.S. Pat. Nos. 7,057,050, 6,488,868, 5,756,004 and WO 2003042428 A1. However, due to their inherent biostatic properties their biotoxicity profile is often unacceptable and the compounds are not readily biodegradable.

Accordingly, there is an ongoing need for new, effective, environmentally friendly corrosion inhibitors which meet the new regulatory criteria.

SUMMARY OF THE INVENTION

In an embodiment, this invention is a quaternary nitrogen-containing corrosion inhibitor of formula

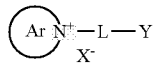

wherein

is an aromatic, nitrogen-containing ring of 5 to 14 ring atoms, optionally containing an additional N, O or S ring atom and optionally substituted with one or more alkyl, alkenyl, aryl, arylalkyl, cycloalkyl, amino, aminoalkyl, alkoxy, hydroxylalkyl, or cyano groups, or a mixture thereof; Y is a group of formula $-OC(O)R_1$ or $-C(O)R_1$; L is $C_1$-$C_{10}$ alkyl, $C_2$-$C_{10}$ alkenyl or a group of formula $-CH_2CH(OR_2)CH_2-$; $R_1$ is $C_8$-$C_{20}$ alkyl or $C_8$-$C_{20}$ alkenyl; $R_2$ is H or $-C(O)R_1$; $R_3$ and $R_4$ are independently selected from H, alkyl, alkenyl, amino, alkoxy, hydroxylalkyl and cyano; and X is Br, Cl or I.

The corrosion inhibitors of the invention have a lower environmental impact when compared to existing commercial treatments by virtue of their low toxicity, higher biodegradation and lower bioaccumulation. In addition, the corrosion inhibitors of this invention are less volatile, hence less malodorous than existing alkylpyridine corrosion inhibitors.

DETAILED DESCRIPTION

As used herein, "Alkenyl" means a monovalent group derived from a straight or branched hydrocarbon containing at least one carbon-carbon double bond by the removal of a single hydrogen atom. Alkenyl groups include, for example, ethenyl, propenyl, butenyl, 1-methyl-2-buten-1-yl and the like.

"Alkoxy" means an alkyl group, as defined above, attached to the parent molecular moiety through an oxygen atom. Representative alkoxy groups include methoxy, ethoxy, propoxy, butoxy, and the like.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, and the like.

"Alkylene" means a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

"Amino" means a group having the structure $-NR'R''$ wherein R' and R'' are independently selected from H and alkyl, as previously defined. Additionally, R' and R'' taken together may optionally be $-(CH_2)_k-$ where k is an integer of from 2 to 6. Representative amino groups include, amino ($-NH_2$), methylamino, ethylamino, n- and iso-propylamino, dimethylamino, methylethylamino, piperidino, and the like.

"Aminoalkyl" means an alkyl group as defined herein substituted by one or more amino groups as defined herein. Representative aminoalkyl groups include aminomethyl, dimethylaminomethyl, diethylaminomethyl, 2-aminoethyl, 2-dimethylaminoethyl, 2-ethylaminoethyl, and the like.

"Aryl" means substituted and unsubstituted aromatic carbocyclic radicals and substituted and unsubstituted heterocyclic radicals having about 5 to about 14 ring atoms. Representative aryl include phenyl naphthyl, phenanthryl, anthracyl, pyridyl, furyl, pyrrolyl, quinolyl, thienyl, thiazolyl, pyrimidyl, indolyl, and the like. The aryl is optionally substituted with one or more groups selected from hydroxy, halogen, $C_1$-$C_4$ alkyl and $C_1$-$C_4$ alkoxy.

"Arylalkyl" means an aryl group attached to the parent molecular moiety through an alkylene group. Representative arylalkyl groups include benzyl, phenethyl, napth-1-ylm-ethyl, phenylpropyl, and the like.

"Cycloalkyl" means a non-aromatic ring system of about 5 to about 10 carbon atoms, preferably of about 5 to about 10 carbon atoms. The cycloalkyl optionally contains an additional N, O or S ring atom. Preferred ring sizes of rings of the ring system include about 5 to about 6 ring atoms. The cycloalkyl is optionally substituted with one or more groups selected from hydroxy, halogen, $C_1$-$C_4$ alkyl and $C_1$-$C_4$ alkoxy. Representative cycloalkyl include cyclopentyl, cyclohexyl, cycloheptyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Fused cycloalkyl" means a cycloalkyl in which at least two of the ring atoms of the cycloalkyl are also atoms contained in the ring system of the aromatic, nitrogen containing ring of the corrosion inhibitor of this invention.

"Hydroxyalkyl" means an alkyl group as defined herein substituted with one or more hydroxyl (—OH) groups. Representative hydroxyalkyl groups include hydroxymethyl, 2-hydroxyethyl, 2-hydroxypropyl, and the like.

The preparation of representative inhibitors of this invention where L is —$CH_2CH(OR_2)CH_2$— is shown in Scheme 1.

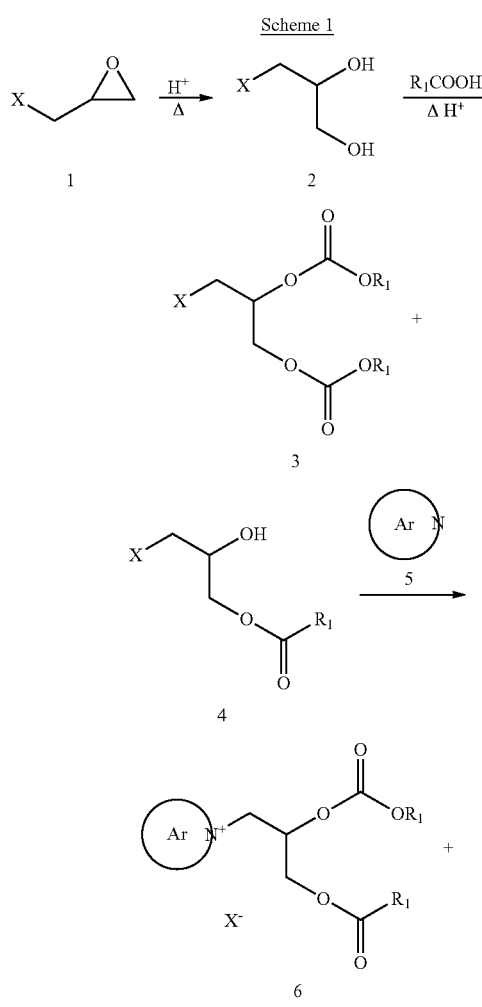

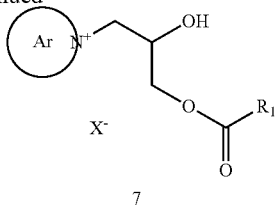

As shown in Scheme 1, 1-halo-2,3-dihydroxypropane 2 is prepared by ring opening of epihalohydrin 1, where X is Br, Cl or I, in the presence of catalytic acid such as HCl. Condensation of 2 with long chain fatty acids $R_1CO_2H$, where $R_1$ is defined herein at a temperature of about 100 to about 170° C. results in formation of a mixture of mono- and bis-haloester derivatives 3 and 4. Heating the mixture of haloesters 3 and 4 at a temperature of about 100 to about 160° C. with the aromatic, nitrogen containing ring compound 5, for example at about 150° C. for 2 hours, results in formation of a mixture of inhibitors 6 and 7.

The preparation of representative inhibitors of this invention where L is $C_1$-$C_{10}$ alkylene or $C_2$-$C_{10}$ alkenylene is shown in Scheme 2.

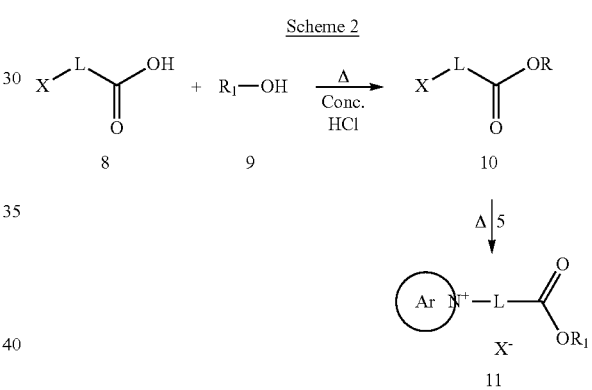

As shown in Scheme 2, long chain haloester 10 where X and $R_1$ are defined herein may be prepared by esterification of haloacid 8, with long-chain alcohol 9, for example by heating a mixture of 8 and 9 at a temperature of about 110 to about 140° C. in the presence of a catalytic acid such as HCl. Reaction of haloester 10 with the aromatic, nitrogen containing ring compound 5 as described in Scheme 1 above results in formation of inhibitor 11.

Representative long chain fatty acids $R_1CO_2H$ include caprylic acid, nonanoic acid, capric acid, undecanoic acid, lauric acid, tridecanoic acid, myristic acid, palmitoleic acid, tall oil fatty acid (mixture of oleic, linoleic and linolenic acids), stearic acid, palmitic acid, arachidic acid, arachidonic acid, oleic acid, 9,11,13-octadecatrienoic acid, 5,8,11,14-eicosatetraenoic acid, eicosenoic acid, heneicosenoic acid, erucic acid, heneicosanoic acid, behenic acid, 3-methylhexadecanoic acid; 7-methylhexadecanoic acid, 13-methylhexadecanoic acid; 14-methyl-11-eicosenoic acid, and the like and mixtures thereof.

In an embodiment, the fatty acid is tall oil fatty acid.

In an embodiment, the fatty acid is lauric acid.

Representative aromatic nitrogen-containing ring compounds 5 include substituted and unsubstituted oxazole, thiazole, acridine, cinnoline, quinoxazoline, pyridazine, pyridine, pryimidine, quinazolinie, quinoline and isoquinoline. The ring compounds may be unsubstituted or substituted with 1-4 substituents independently selected from alkyl, alkenyl, aryl, arylalkyl, cycloalkyl, amino, aminoalkyl, alkoxy, hydroxylalkyl, and cyano, or a mixture thereof.

In an embodiment, the aromatic nitrogen-containing ring compounds are selected from pyridine and quinoline.

Representative substituted pyridine and quinoline rings include 4-methylpyridine, 2-methylpyridine, 2-methyl-3,5-diethylpyridine, 3-ethyl-4-methylpyridine, 2-methyl-5-(but-2-enyl)pyridine, 2-(prop-1-enyl)-5-ethylpyridine, 2-vinylpyridine, 4-vinylpyridine, 3-pyridiylcarbinol, 3-methylpyridine, 3,5-diethyl-1,2-dihydro-1-phenyl-2-propylpyridine, 2,6-dimethylpyridine, 3-cyanopyridine, 2-cyanopyridine, 2,3,5-trimethylpyridine, 2,4,6-trimethylpyridine, 2-amino-3-methylpyridine, 2-aminopyridine, 2-methyl-5-(2-ethylaminoethyl)pyridine, 2,4-dimethylquinoline, 2,6-dimethylquinoline, 2,7-dimethylquinoline, 4-methoxy-2-phenylquinoline, 2-(3,4-methylenedioxyphenylethyl)quinoline, 2-n-propylquinoline, 2-(prop-1-enyl)quinoline, 4-methoxy-2-n-pentylquinoline, chimamine, cusparine, skimmianine, chinanine, 4-aminoquinoline, 4-methyl-2-phenylquinoline, and the like.

In an embodiment, the pyrindine and quinoline rings are substituted with 1-4 $C_1$-$C_6$ alkyl or $C_2$-$C_6$ alkenyl, $C_1$-$C_6$ aminoalkyl groups, or a mixture thereof.

In an embodiment, the quaternary nitrogen compound of the invention has formula

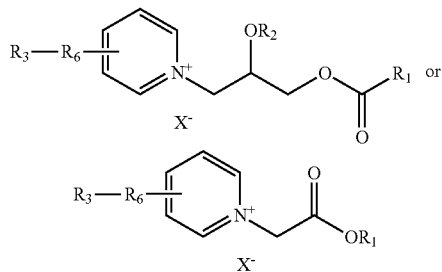

where X and n are defined herein and $R_3$-$R_6$ are independently selected from H, alkyl, alkenyl, aryl, arylalkyl, amino, aminoalkyl, alkoxy, hydroxylalkyl, and cyano groups, or a mixture thereof, or any two of $R_3$-$R_6$ taken together with the ring atoms to which they are attached may form a fused cycloalkyl or fused heterocyclyl ring. It should be noted that in the foregoing structures, the solid lines to the groups $R_3$-$R_6$ are intended to indicate that $R_3$-$R_6$ may be attached to any carbon atom in the pyridine ring.

In an embodiment, the quaternary nitrogen compound has formula

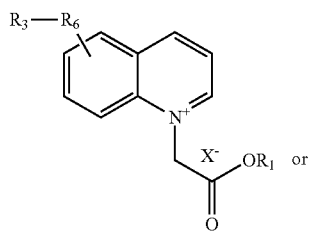

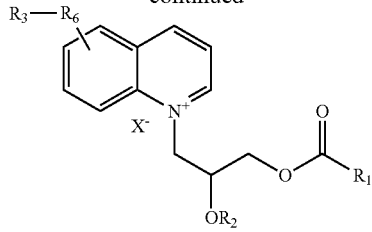

where X and n are defined herein and $R_3$-$R_6$ are independently selected from H, alkyl, alkenyl, aryl, arylalkyl, amino, aminoalkyl, alkoxy, hydroxylalkyl, and cyano groups, or a mixture thereof, or any two of $R_3$-$R_6$ taken together with the ring atoms to which they are attached may form a fused cycloalkyl or fused heterocyclyl ring. It should be noted that in the foregoing structures, the solid lines to the groups $R_3$-$R_6$ are intended to indicate that $R_3$-$R_6$ may be attached to any carbon atom in the quinoline ring system.

The quaternary nitrogen-containing corrosion inhibitor of the present invention can be used in any system exposed to fluids (i.e., liquid, gas, slurry or mixture thereof) containing a metal corrosion agent where improved corrosion inhibition is desired. However, the corrosion inhibitors of the present invention are particularly well-suited for use in oil and gas field applications and refinery operations.

With respect to such oil and gas field applications, the corrosion inhibitor of the present invention may be added to oil and/or gas fluids in the form of a solution or dispersion in one or more organic solvents or a mixture of water and organic solvent. Examples of suitable solvents are alcohols such as methanol, ethanol, isopropanol, isobutanol, secondary butanol, glycols such as ethylene glycol, and ethylene glycol monobutyl ether ("EGMBE"), and the like, and aliphatic and aromatic hydrocarbons including heavy aromatic naphtha. The selection of the solvent system may be made empirically based on the characteristics of the system being treated and the particular corrosion inhibitor(s) used. For example, the corrosion inhibitors are typically sparingly soluble or insoluble in water, but may be suitably formulated in a mixture of water and one or more alcohols or glycols. Similarly, the corrosion inhibitors may be suitably formulated in heavy aromatic naphtha by incorporating one or more alcohols or glycols in the composition.

In an embodiment, the organic solvents comprise ethylene glycol monobutyl ether.

The amount of active ingredient in a corrosion inhibitor formulation required to sufficiently reduce the rate of corrosion varies with the system in which it is used. Methods for monitoring the severity of corrosion in different systems are well-known to those skilled in the art, and may be used to decide the effective amount of active ingredient required in a particular situation. The compounds may be used to impart the property of corrosion inhibition to a composition for use in an oil or gas field application and may have one or more functions other than corrosion inhibition, e.g. scale inhibition.

In an embodiment, this invention is a corrosion inhibitor composition comprising 5 to 50 weight percent of one or more quaternary nitrogen-containing corrosion inhibitors according to the invention dispersed or dissolved in one or more organic solvents.

In an embodiment, the corrosion inhibitor composition comprises 5 to 20 weight percent of the quaternary nitrogen-containing corrosion inhibitors.

The quaternary nitrogen-containing corrosion inhibitors described herein have proven to be particularly effective for inhibiting corrosion of mild steel in hydrocarbon, oil/brine mixtures and aqueous systems under a variety of conditions. The inhibitors claimed herein are useful in both sour systems, i.e., systems having a relatively high $H_2S$ concentration and sweet systems, i.e., systems having a relatively high $CO_2$ concentration. In the case of sweet systems, the inhibitors are advantageously used in combination with a sulphur-containing material such as 2-mercaptoethanol, sodium thiosulfate, thioglycolic acid and alkyl thiols.

Although fluid content of flow lines may vary, the inhibitor may be used in a variety of environments. Oil cuts in the field can range from less than 1% (oil field) to 100% (refinery) oil, while the nature of the water can range from 0 to 300,000 ppm TDS (total dissolved solids). In addition, the inhibitors of the present invention are also useful in large diameter flow lines of from about 1 inch to about 4 feet in diameter, small gathering lines, small flow lines and headers. In a preferred method, the inhibitor is added at a point in the flow line upstream from the point at which corrosion prevention is desired.

In practice, the inhibitors of the present invention are preferably added to the flow line continuously to maintain a corrosion inhibiting dose of from about 0.01 to about 5000 ppm. More preferably, the corrosion inhibiting dose is from about 0.1 to about 500 ppm. In a most preferred embodiment of the present invention, the corrosion inhibiting dose is from about 1 to about 250 ppm. Although a most preferred use of the corrosion inhibitors of the present invention is for mild steel flow lines, it is believed that the inhibitors are also effective in inhibiting corrosion in other types of metallurgy. In certain cases, batch treatments are the method of choice for application of the inhibitors of the present invention. However, the invention can also be practiced using a continuous process. Dosage rates for batch treatments range from about 0.1. to about 50,000 ppm. In a preferred embodiment of the present invention, the flow rate of the flow line in which the inhibitor composition is used is between 0 and 100 feet per second. A more preferred flow rate is between 0.1 and 50 feet per second.

The inhibitors of the present invention may be used alone or in combination with other compounds. Typical formulations include pour point depressants and/or surfactants. Examples of suitable pour point depressants are $C_1$ to $C_3$ linear or branched alcohols, ethylene and propylene glycol. Examples of suitable surfactants are ethoxylated nonylphenols and/or ethoxylated amines as wetting agents or additives for dispersing the inhibitor into the fluid stream to which they are added. The surfactant is advantageously water soluble to allow the product to better wet the surface of the flow line where corrosion may take place. Water soluble surfactants utilized may be non-ionic, cationic or anionic and will generally have a hydrophilic-lipophilic (HLB) value of about 1. Oil soluble surfactants may be utilized if it is desired to disperse the inhibitor composition into a hydrocarbon fluid. Oil soluble surfactants may be non-ionic, cationic or anionic. These surfactants typically have an HLB value less than 7.

Other compounds which may also be blended with the inhibitors include quaternary amines, such as fatty, cyclic or aromatic amines quaternized with lower alkyl halides or benzyl chloride and certain amides. In addition, formulations including the inhibitors of the present invention may include filming agents such as p-toluenesulfonic acid and dodecylbenzenesulfonic acid. Formulations including inhibitors of the present invention may also include filming agents such as imidazolines and/or mono or bis phosphate esters. The corrosion inhibitor may also contain components which are typically included in corrosion inhibiting compositions, such as scale inhibitors, demulsifiers, and/or surfactants. In some instances, it may be desirable to include a biocide in the composition.

The formulation is preferably produced by blending the ingredients into a homogeneous mixture.

The resultant inhibitor formulation may be used in a variety of petroleum operations in the oil and gas industry. It can be used to treat systems used in primary, secondary and tertiary oil and gas recovery. The inhibitor formulation may be introduced to such systems in accordance with techniques well-known to those skilled in the art. For example, one technique in which the inhibitor formulation can be used is the squeeze treating technique, whereby the inhibitor formulation is injected under pressure into a producing formation, adsorbed onto the strata and absorbed as the fluids are produced. The inhibitor formulation can further be added in water flooding operations of secondary oil recovery, as well as be added to pipelines, transmission lines and refinery units. The inhibitor formulation may also be used to inhibit acid solution in well-acidizing operations.

The foregoing may be better understood by reference to the following Examples, which are presented for purposes of illustration and are not intended to limit the scope of the invention.

EXAMPLE 1

Epichlorohydrin (34 g, 0.36 m) is heated at 80° C. with a catalytic amount of concentrated hydrochloric acid (1 ml) for 20 minutes to open the ring and obtain 1-chloro-2,3-dihydroxy-propane. This is condensed with 1.5 equiv. of tall oil fatty acids (155 g, 0.55 m) at 150° C. for 3 hours to obtain a mixture of mono and bis esters. Any residual hydrochloric acid is neutralised with solid sodium bicarbonate. Substituted pyridine (Alkolidine 12, available from Lonza Ltd., Basel, Switzerland, 95 g, 0.55 m) is added and the reaction mixture is heated at 150° C. for 2 hours to obtain the corresponding substituted pyridinium salt. Sodium chloride is filtered off and any other inorganics are removed by dissolving in water. Yield: 260 g.

EXAMPLE 2

Chloroacetic acid (20 g, 0.211 m) is heated with n-octanol (28 g, 0.22 m) at 120° C. for 2 hours in the presence of a catalytic amount of concentrated hydrochloric acid. The reaction mixture is allowed to cool and substituted pyridine (Alkolidine 12, 42 g, 0.22 m) is added. The reaction mixture is heated at 130° C. for another 2 hours to provide the substituted alkyl pyridinium ester. Yield 86 g.

EXAMPLE 3

Performance Testing

Standard Linear Polarisation Resistance (LPR) techniques in a 'bubble' or stirred kettle assembly are used to measure the instantaneous corrosion rate in the brine solution as a function of time. Synthetic seawater (deionised water containing 3% sodium chloride) saturated with $CO_2$ and de-aromatised kerosene (LVT-200) are used in a 90:10 ratio at 60° C.

An automated electrochemical measurement system (ACM Instruments Gill 12) and associated software is used to conduct electrochemical measurements. Three pin probes constructed from type C1018 mild steel are used for all bubble test and Rotating Cylinder Electrode (RCE) measurements. Standard ranges of concentrations are examined to generate performance concentration curves in an environment where the inhibitor species has been allowed to partition. A blank corrosion rate for each cell is measured every 10 minutes for two hours whereupon chemical injection is made into the hydrocarbon phase. The corrosion rate is then continuously measured for a subsequent 18 hours. RCE complements LPR by virtue of its ability to generate a moderate shear stress (10 Pa) in the solution, which is $CO_2$ sparged synthetic brine (deionised water containing 3% sodium chloride) at 60° C.

LPR Bubble and RCE Testing

Corrosion inhibitor performances are initially investigated using LPR bubble tests where general corrosion rates of type C1018 steel electrodes are measured in $CO_2$ sparged synthetic brine and dearomatised kerosene mixture (90:10) for 18 hours at 60° C. in the presence of corrosion inhibitors.

In the data shown below, Inhibitor 1 is an alkyl quinolinium-based corrosion inhibitor comprising a mixture of mono- and disubstituted esters of lauric acid. Inhibitor 2 is an alkyl quinolinium-based corrosion inhibitor comprising a mixture of mono- and disubstituted esters of tall oil fatty acid. Inhibitor 3 is an alkyl pyridinium-based corrosion inhibitor comprising a mixture of mono- and disubstituted esters of lauric acid. Inhibitor 4 is an alkyl pyridinium-based corrosion inhibitor comprising a mixture of mono- and disubstituted esters of tall oil fatty acid. Inhibitors 1-4 are prepared according to the method of Example 1.

The inhibitors are formulated in compositions consisting of inhibitor (20 weight percent), thioglycolic acid (20 weight percent) and EGMBE (60 weight percent). Corrosion protection results are presented in Table 1.

TABLE 1

| Inhibitor | Corrosion protection (%) after 18 hrs | | | |
|---|---|---|---|---|
| | 2.5 ppm | 5 ppm | 10 ppm | 25 ppm |
| Commercial alkyl pyridine[1] | 94 | 96 | 96 | 98 |
| 4 | 91 | 95 | 96 | 97 |
| 3 | 88 | 90 | 91 | 98 |
| 1 | 97 | 97 | 99 | 99 |
| 2 | 91 | 96 | 97 | 98 |

[1]Alkolidine 12, Lonza Ltd., Basel, Switzerland.

As shown in Table 1, formulations comprising representative inhibitors of the invention provide corrosion protection comparable to a commercially available alkyl pyridine corrosion inhibitor over a range of dosages.

The general corrosion rate before and after the addition of inhibitors at a concentration of 25 ppm is shown in Table 2.

TABLE 2

| Inhibitor | Corrosion Protection (%) | Pre-Corrosion Rate (mmpy) | Inhibited Corrosion Rate (mmpy) |
|---|---|---|---|
| Commercial alkyl pyridine[1] | 98 | 6.350 | 0.127 |
| 2 | 97 | 6.526 | 0.192 |
| 3 | 98 | 6.163 | 0.128 |

[1]Alkolidine 12, Lonza Ltd., Basel, Switzerland.

The inhibitor performances are further assessed by RCE. A summary of RCE test results is shown in Table 3.

TABLE 3

| Inhibitor | Corrosion Protection (%) | Pre-Corrosion Rate (mmpy) | Inhibited Corrosion Rate (mmpy) |
|---|---|---|---|
| Commercial alkyl pyridine[1] | 96 | 9.846 | 0.384 |
| 4 | 95 | 5.666 | 0.292 |
| 3 | 94 | 9.344 | 0.556 |

[1]Alkolidine 12, Lonza Ltd., Basel, Switzerland.

As shown in Tables 2 and 3, corrosion rates in the presence of representative inhibitors of this invention and commercial alkyl pyridine corrosion inhibitors are comparable.

EXAMPLE 4

Emulsification Tendency Testing

Corrosion inhibitor injected into produced fluids will concentrate to some extent in the water phase but a significant portion will reside at oil/water interface. High concentrations of corrosion inhibitor can cause significant emulsion problems. Screening is carried out to assess the emulsification tendency of inhibitors in presence of de-aromatised kerosene (LVT-200).

The test procedure used involves mixing synthetic hydrocarbon LVT-200 and brine in glass bottles and the addition of corrosion inhibitor at a concentration that is huge excess to that which is actually applied in the field, i.e., 100, 200 and 500 ppm. After addition of the corrosion inhibitor, the bottles are shaken for 2 minutes and visual assessment is made at time intervals of 2, 5, and 10 minutes and compared with the blank, which does not contain any inhibitor.

Comparison of emulsification tendency of representative Inhibitor 2 and a commercial alkyl pyridine reveals that Inhibitor 1 and the commercial inhibitor behave comparably with respect to water quality.

EXAMPLE 5

Environmental Profiles

The environmental impact of a production chemical is typically defined by three tests: biodegradation, bioaccumulation and toxicity. All three criteria have limits that must be achieved in order for a chemical to be permitted for use. In order for a product to be used without restriction offshore, two of the following three criteria must be satisfied[1]:

Biodegradation must be greater than 60% (if less than 20% material is automatically marked for substitution)

Bioaccumulation as measured by Octanol/Water partitioning coefficient ($LogP_{o/w}$) must be below 3 (or molecular weights higher than 700)

Toxicity to the most sensitive marine species (typically Skeletonema) must be greater than $LC_{50}$ or $EC_{50}$ of 10 ppm.

Three environmental screens are performed to measure toxicity, bioaccumulation and biodegradation of the corrosion inhibitors. The environmental profile of existing and modified inhibitors is shown in Table 4 below.

TABLE 4

| Inhibitor | Toxicity EC$_{50}$ (ppm) | Bioaccumulation LogP$_{o/w}$(Mol. Wt.) | Biodegradation, t = 28 days |
|---|---|---|---|
| Green | >10 | <3 (or Mw > 700) | >60% |
| Commercial alkyl pyridine[1] | 3.3 | 2.67 | <20% |
| 2 | 23 | Mw > 700 | 50%* |
| 3 | >25 | Mw > 700 | — |

[1]Alkolidine 12, Lonza Ltd., Basel, Switzerland.

As shown in Table 4, Inhibitor 2 meets all the requirements to qualify as a "Green" corrosion inhibitor unlike the parent compound alkyl pyridine. Similarly Inhibitor 3 has a much improved environmental profile compared to alkyl pyridine which fails to qualify as "Green" inhibitor due to less than 20% biodegradation after 28 days in sea water.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of inhibiting corrosion of a metallic surface in contact with a fluid in oil and gas applications comprising adding to the fluid an effective corrosion-inhibiting amount of one or more quaternary nitrogen-containing corrosion inhibitors according to the following formula:

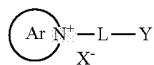

wherein

is an aromatic, nitrogen-containing ring selected from oxazole, thiazole, acridine, cinnoline, quinoxazoline, pyridazine, pyridine, pyrimidine, quinazoline, quinoline, isoquinoline, and mixtures thereof;
Y is a group of formula —OC(O)R$_1$ or —C(O)OR$_1$;
L is —CH$_2$CH(OR$_2$)CH$_2$—;
R$_1$ is C$_8$-C$_{20}$ alkyl or C$_8$-C$_{20}$ alkenyl;
R$_2$ is H or —C(O)R$_1$; and
X is Br, Cl or I.

2. The method of claim 1, wherein the quaternary nitrogen-containing corrosion inhibitors have the formula:

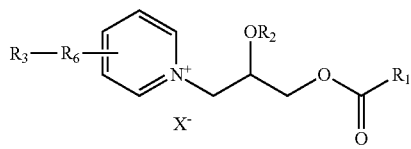

wherein R$_3$-R$_6$ are independently selected from H alkyl, alkenyl, aryl, arylalkyl, cycloalkyl, amino, aminoalkyl, alkoxy, hydroxylalkyl, or cyano groups, or a mixture thereof, or any two of R$_3$-R$_6$ taken together with the ring atoms to which they are attached may form a fused cycloalkyl.

3. The method of claim 2, wherein R$_3$-R$_6$ are independently selected from H, C$_1$-C$_6$ alkyl, C$_2$-C$_6$ alkenyl, or C$_1$-C$_6$ aminoalkyl, or a mixture thereof.

4. The method of claim 1, wherein the corrosion inhibitor compound is added in a composition comprising 5 to 50 weight percent of the one or more quaternary nitrogen-containing corrosion inhibitors dispersed or dissolved in one or more organic solvents.

5. The method of claim 4, wherein the organic solvents are selected from alcohols, glycols and aliphatic and aromatic hydrocarbons.

6. The method of claim 5, wherein the organic solvents comprise ethylene glycol monobutyl ether.

7. The method of claim 6, comprising 5 to 20 weight percent of the one or more quaternary nitrogen-containing corrosion inhibitors.

8. The method of claim 1, wherein the fluid comprises oil or gas and water.

9. A method of inhibiting corrosion of a metallic surface in contact with a fluid in oil and gas applications comprising adding to the fluid an effective corrosion-inhibiting amount of one or more quaternary nitrogen-containing corrosion inhibitors according to the following formula:

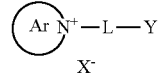

wherein

is an aromatic, nitrogen-containing ring, wherein the nitrogen-containing ring is a pyridine or quinoline substituted with 1-4 C$_1$-C$_6$ alkyl, C$_2$-C$_6$ alkenyl, or C$_1$-C$_6$ aminoalkyl groups, or a mixture thereof;
Y is a group of formula —OC(O)R$_1$ or —C(O)OR$_1$;
L is C$_1$-C$_{10}$ alkylene, C$_2$-C$_{10}$ alkenylene or a group of formula —CH$_2$CH(OR$_2$)CH$_2$—;
R$_1$ is C$_8$-C$_{20}$ alkyl or C$_8$-C$_{20}$ alkenyl;
R$_2$ is H or —C(O)R$_1$; and
X is Br, Cl or I.

10. The method of claim 9, wherein L is C$_1$-C$_{10}$ alkylene or C$_2$-C$_{10}$ alkenylene.

11. The method of claim 10, wherein L is methylene.

12. The method of claim 9, wherein the corrosion inhibitor compound is added in a composition comprising 5 to 50 weight percent of the one or more quaternary nitrogen-containing corrosion inhibitors dispersed or dissolved in one or more organic solvents.

13. The method of claim 12, wherein the organic solvents are selected from alcohols, glycols and aliphatic and aromatic hydrocarbons.

14. The method of claim 13, wherein the organic solvents comprise ethylene glycol monobutyl ether.

15. The method of claim 14, comprising 5 to 20 weight percent of the one or more quaternary nitrogen-containing corrosion inhibitors.

16. The method of claim 9, wherein the fluid comprises oil or gas and water.

17. A method of inhibiting corrosion of a metallic surface in contact with a fluid in oil and gas applications comprising adding to the fluid an effective corrosion-inhibiting amount of one or more quaternary nitrogen-containing corrosion inhibitors having the formula:

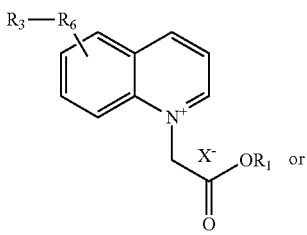 or

-continued

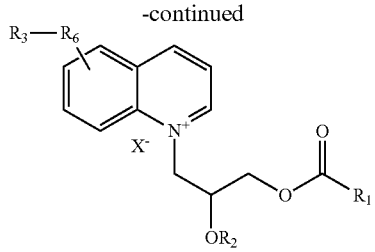

wherein $R_3$-$R_6$ are independently selected from H, alkyl, alkenyl, aryl, arylalkyl, cycloalkyl, amino, aminoalkyl, alkoxy, hydroxylalkyl, or cyano groups, or a mixture thereof, or any two of $R_3$-$R_6$ taken together with the ring atoms to which they are attached may form a fused cycloalkyl or fused heterocyclyl ring;

X is Br, Cl, or I;

$R_1$ is $C_8$-$C_{20}$ alkyl or $C_8$-$C_{20}$ alkenyl; and $R_2$ is H or —C(O)$R_1$.

18. The method of claim 17, wherein $R_3$-$R_6$ are independently selected from H, $C_1$-$C_6$ alkyl, $C_2$-$C_6$ alkenyl, or $C_1$-$C_6$ aminoalkyl, or a mixture thereof.

* * * * *